United States Patent
Świętoslawski

(10) Patent No.: US 11,382,664 B2
(45) Date of Patent: Jul. 12, 2022

(54) DEVICE FOR NEUTRALIZING ECTOPARASITES

(71) Applicant: ICB PHARMA SPÓŁKA JAWNA Tomasz Świętoslawski, Paweł Świętoslawski, Jaworzno (PL)

(72) Inventor: Tomasz Świętoslawski, Jaworzno (PL)

(73) Assignee: ICB PHARMA SPOLKA JAWNA TOMASZ SWIETOSLAWSKI, PAWEL SWIETOSLAWSKI, Jaworzno (PL)

( * ) Notice: Subject to any disclaimer, the term of this patent is extended or adjusted under 35 U.S.C. 154(b) by 250 days.

(21) Appl. No.: 16/633,709

(22) PCT Filed: Jul. 24, 2018

(86) PCT No.: PCT/PL2018/000074
§ 371 (c)(1),
(2) Date: Jan. 24, 2020

(87) PCT Pub. No.: WO2019/022626
PCT Pub. Date: Jan. 31, 2019

(65) Prior Publication Data
US 2020/0205858 A1    Jul. 2, 2020

(30) Foreign Application Priority Data
Jul. 24, 2017    (PL) .......................... 422338

(51) Int. Cl.
*A61B 17/50* (2006.01)
*A01M 3/00* (2006.01)
*B65D 83/38* (2006.01)

(52) U.S. Cl.
CPC .............. *A61B 17/50* (2013.01); *A01M 3/00* (2013.01); *B65D 83/386* (2013.01); *A61B 2017/505* (2013.01)

(58) Field of Classification Search
CPC .... A61B 2017/505; A61B 17/50; A01M 3/00; A01M 7/0017; B65D 83/386
See application file for complete search history.

(56) References Cited

U.S. PATENT DOCUMENTS 3,306,252 A * 2/1967 Knight .................. B65D 83/22
                                                    118/710
5,462,556 A * 10/1995 Powers .................. A61B 17/50
                                                    119/651

(Continued)

FOREIGN PATENT DOCUMENTS

DE    20012032 U1    11/2000
DE    20305694 U1    9/2004

(Continued)

OTHER PUBLICATIONS

International Search Report and Written Opinion, PCT/PL2018/000074, dated Oct. 30, 2018, 8 pages.

(Continued)

*Primary Examiner* — J C Jacyna
(74) *Attorney, Agent, or Firm* — Ware, Fressola, Maguire & Barber LLP

(57) ABSTRACT

The present invention relates to a device (1) for neutralizing ectoparasites. In order to prevent a release of toxic substances into a host body by an ectoparasite during its removal the device comprises a container (3) containing a neutralizing freezing medium, preferably an aerosol cooling medium, in particular preferably an aerosol of a mixture of isohexadecane, isopropyl myristate and cooling medium, preferably 1,1,1,2-tetrafluoroethane; a body (2), in which the container (3) is located and which comprises a terminal front wall (21) with a discharge opening (212) located on the axis (O) of the outlet (31) of the container (3) and a terminal rear wall (22); a body end part (23) in a form of a convex shell element that encloses the discharge opening (212) of the (Continued)

terminal front wall (21) on the external side of this wall (21) and comprises an exhaust opening (231) located on the axis (O) of the discharge opening (212) of the terminal front wall (21) at a distance from this discharge opening (212) and at least one vent opening (232).

20 Claims, 2 Drawing Sheets

(56) References Cited

U.S. PATENT DOCUMENTS

| | | | | |
|---|---|---|---|---|
| 6,113,008 | A * | 9/2000 | Arsenault | A61M 35/003 |
| | | | | 239/337 |
| 9,380,774 | B2 * | 7/2016 | Gellani | A01M 1/2038 |
| 2006/0271069 | A1 | 11/2006 | Glaesel | |
| 2007/0112379 | A1 * | 5/2007 | Vaic | A61B 17/50 |
| | | | | 606/211 |
| 2010/0191252 | A1 * | 7/2010 | Herweijer | A61B 17/50 |
| | | | | 606/131 |
| 2017/0361012 | A1 * | 12/2017 | Parker | A61M 1/815 |

FOREIGN PATENT DOCUMENTS

| | | |
|---|---|---|
| PL | 61849 Y1 | 2/2004 |
| PL | 61843 Y1 | 4/2004 |
| WO | 2008093372 A1 | 8/2008 |
| WO | 2016178161 A1 | 11/2016 |

OTHER PUBLICATIONS

International Preliminary Report on Patentability, PCT/PL2018/000074, dated Oct. 8, 2019, 20 pages.

* cited by examiner

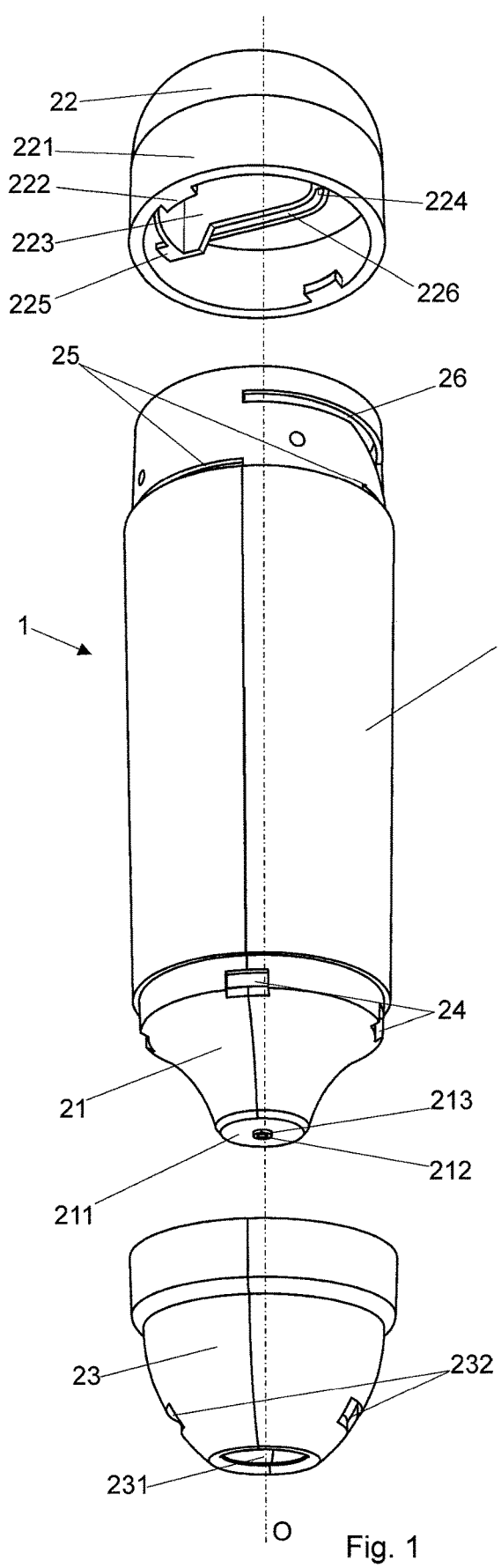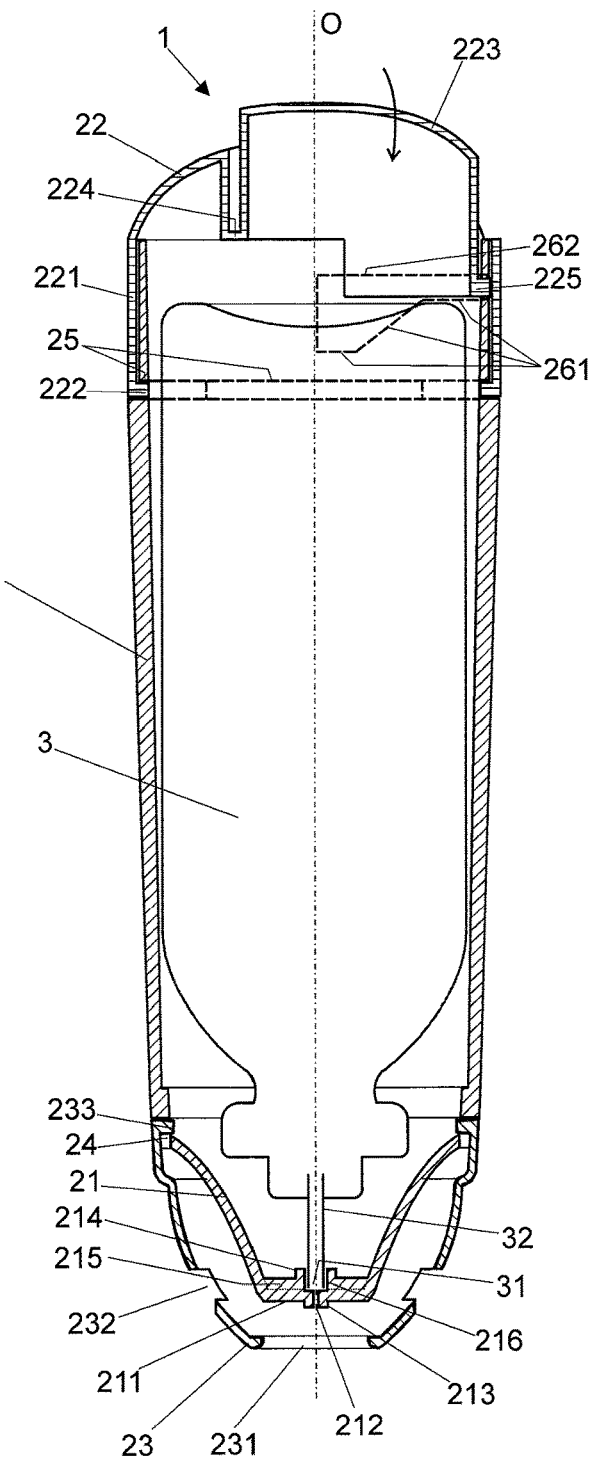
Fig. 1
Fig. 2

DEVICE FOR NEUTRALIZING ECTOPARASITES

The invention relates to a device for neutralizing ectoparasites, in particular ticks.

BACKGROUND OF THE INVENTION

Various devices and tools for removing ectoparasites buried into the host body are known from the state of art.

For example Polish patent application P.377776 discloses a tool for removing ectoparasites from a skin which has a V-shaped groove with side surfaces converging towards each other from an outer opening at the edge to an inner convergence point, wherein the V-shaped groove is wider at the top surface of the catching part than at the bottom side. An essential part of each side surface of the V-shaped groove between the bottom surface and the top face of the catching part is a concave catching surface.

Polish utility model application W.113425 discloses a device provided with arms for extracting ectoparasites out, which is characterized in that in its housing a sleeve is slidably embedded, inside of which a tank is mounted, wherein below the tank a body is located provided with a valve at the top and with four elastic arms at the bottom, wherein in one of the elastic arms a channel is provided through which a disinfectant is delivered from the container. In the top part of the device, a spring is mounted on the sleeve, which rests against a sleeve flange at the top and against the housing at the bottom.

Another exemplary device is known from Polish utility model application W.113562 disclosing a device for removing ectoparasites by means of a suction, which also enables sucking out parasitic venom. The device comprises a cylindrical body having one end open and the other end is coupled with a suction end part by means of a separating bottom provided with a through-hole. Inside the body there is a piston which is ended with a rubber gasket.

Publication DE 200 12 032 U1 discloses a device for removing ectoparasites from skin comprising a container containing a freezing medium, a body in which container is located, and an integrated releasing mechanism.

It is widely known that during a removal of an ectoparasite buried into a skin, the ectoparasite usually rapidly evacuates to a host body a number of dangerous substances, such as various pathogens and neurotoxins. A major drawback of the prior art solutions is that they do not protect against a delivery of these substances into a host body by an ectoparasite.

Therefore, it has been the object of the present invention to provide a device preventing a release of toxic substances into the host body by an ectoparasite during a process of a removal thereof.

SUMMARY OF THE INVENTION

According to the present invention there is provided a device for neutralizing ectoparasites, comprising a container containing a neutralizing freezing medium, a body, in which the container is located, and which comprises a terminal front wall with a discharge opening located on the axis of the container outlet and a terminal rear wall;

a body end part in a form of a convex shell element that encloses the discharge opening of the terminal front wall on the external side of this wall and comprises an exhaust opening located on the axis of the discharge opening of the terminal front wall at a distance from this discharge opening and at least one vent opening, wherein: the terminal rear wall of the body comprises an actuating element provided with a lock, and the terminal rear wall is a separate individual element detachably connected to the body so as to enable rotating the terminal rear wall relative to the body around the longitudinal axis of the body, wherein the locking status of the lock is determined by the angular orientation of the terminal rear wall relative to the body.

The neutralizing freezing medium according to the invention is preferably an aerosol cooling medium. A preferred aerosol is an aerosol of a mixture of isohexadecane, isopropyl myristate and cooling medium, preferably 1,1,1,2-tetrafluoroethane.

The use of the device according to the invention consists in adjoining the body end part with the exhaust opening to a host skin in such a way that an ectoparasite is located inside the exhaust opening and then dispensing the neutralization freezing medium from the container.

The device according to the invention ensures an extremely effective and rapid freezing of an ectoparasite buried into a skin, that immediately prevents the ectoparasite for further excretion of toxic substances into a host body. After neutralizing an ectoparasite with the device according to the invention, it is then possible to physically remove an ectoparasite buried into a skin completely from a host body using any tool. Freezing of an ectoparasite with the device according to the invention also results in a formation of a durable coating on an ectoparasite body that prevents against a rupture of ectoparasite body shells, an effusion of an ectoparasite infected body fluids and a translocation of an ectoparasite intestine contents into mouthparts stuck into a host body during a process of an ectoparasite physical removal.

A construction of the device proposed according to the present invention reliably prevents skin burns with a freezing agent, even in a case of an improper (e.g. extended) release of the neutralizing freezing agent from the container.

The device according to the invention operates in any spatial orientation, making it possible to easily neutralize ectoparasites buried into any part of a body, even in a case of an unaided use of the device by a host.

In some preferred embodiments of the present invention, the outlet of the container is located at the end of a container discharge tube that is situated in a positioning recess formed in the terminal front wall of the body.

Reinforcing elements, preferably reinforcing ribs and/or at least one reinforcing ring, are preferably formed in the terminal front wall over the area around the discharge opening.

According to the present invention, it is preferred that the terminal front wall of the body is convex, preferably has a form of a truncated cone with a concave side surface, and includes a central part with a central discharge opening, wherein the central part is preferably flat, and the body end part has the form of a dome having a truncated top part and a central exhaust opening lying in the plane of the central part of the terminal front wall of the body.

The terminal rear wall of the body comprises an actuating element with a lock, and wherein: the terminal rear wall is a separate individual element detachably connected to the body so as to enable rotating the terminal rear wall relative to the body around the longitudinal axis of the body, wherein the locking status of the lock is determined by the angular orientation of the terminal rear wall relative to the body.

In such embodiments it may be further preferred that the actuating element is arranged in the terminal rear wall and connected to the terminal rear wall by means of a deformable element. The actuating element may advantageously be an integral part of the terminal rear wall connected therewith by means of a material bridge.

The terminal rear wall is a separate individual element connected to the body by detachable connection means, preferably with resistance connection means or catching connection means, that enable rotating the terminal rear wall relative to the body around the longitudinal axis of the body, wherein the locking status of said lock is determined by the angular orientation of the terminal rear wall relative to the body.

BRIEF DESCRIPTION OF DRAWINGS

The invention shall be described and explained below in an exemplary embodiment and in a connection with the attached drawings in which:

FIG. 1 shows an embodiment of the device according to the invention in an axonometric exploded view;

FIG. 2 shows an embodiment of the device according to the invention in a longitudinal section;

DETAILED DESCRIPTION OF PREFERRED EMBODIMENT

Figure 3:
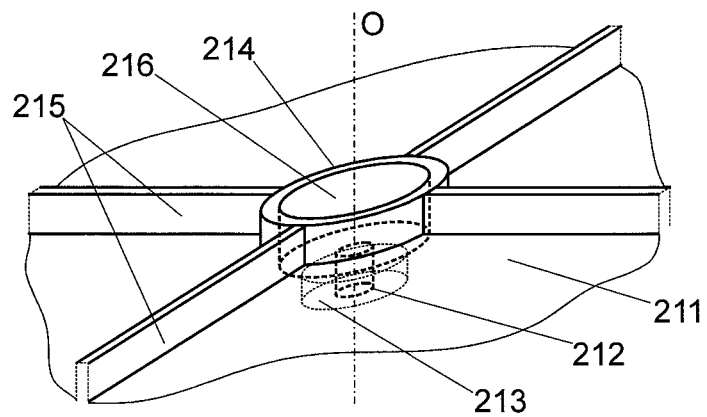
FIG. 3 shows a view of a flat central part of a terminal front wall of the device of FIGS. 1 and 2.
Figure 4:
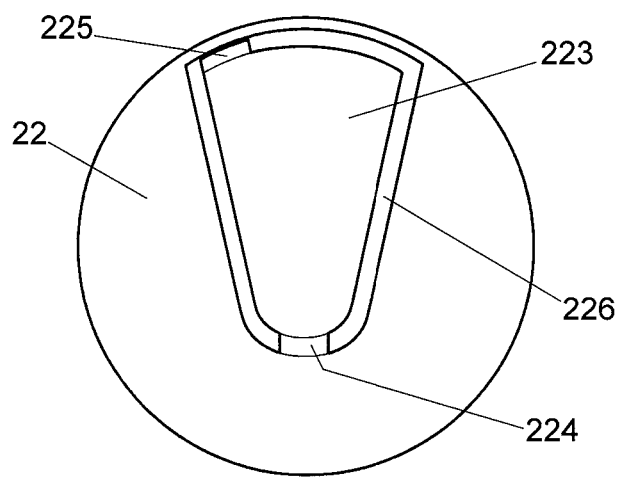
FIG. 4 shows a top view of the terminal rear wall of the device from FIGS. 1 and 2.

The embodiment of the device for neutralizing ectoparasites 1 according to the invention shown in FIGS. 1-4 comprises a cylindrical body 2 with a terminal front wall 21, a terminal rear wall 22 and a body end part 23. The terminal front wall 21 is an integral part of the body 2. The terminal rear wall 22 and the body end cap 23 are separate individual elements connected to the body 2 by means of detachable connection means including catches 222 that project inward from the edge of a sleeve 221 of the terminal rear wall 22 which catches 222 are hooked by corresponding latching openings 25 on the body 2.

Inside the body 2 a pressurized container 3 is embedded having an outlet 31 for an outflow of a neutralizing freezing medium stored in the container 3. The neutralizing freezing medium according to the invention is preferably an aerosol cooling medium. In this embodiment the freezing medium is an aerosol of a mixture of isohexadecane, isopropyl myristate and cooling medium in a form of 1,1,1,2-tetrafluoroethane. The outlet 31 of the container 3 is located at the end of a discharge tube 32 which is an axially displaceable actuating element of a one-way exhaust valve of the container 3. Displacing the discharge tube 32 into the container 3 causes the exhaust valve to became open what results in an outflow of the freezing agent from the container 3 through the tube 32 and the outlet 31. The inner diameter of the body 2 is slightly larger than the outer diameter of the container 3 to allow easy insertion and withdrawal of the container 3 from the body 2.

The longitudinal axes of the body 2, container 3 and its outlet 31 overlap with each other and lie on the longitudinal axis O of the device 1.

The terminal front wall 21 has a form of a convex truncated cone with a concave side surface wherein the outer base of the cone is a flat central part 211 with a circular shape, centered relative to the longitudinal axis O of the body 2 and perpendicular to this axis O.

In the central part 211 of the terminal front wall 21, a discharge opening 212 is formed positioned on the axis O of the outlet 31 of the container 3. Around the discharge opening 212 an external reinforcing ring 213 and an internal reinforcing ring 214 are formed (located respectively on the outer and inner side of the wall 21), wherein from the internal reinforcing ring 214 four equiangularly spaced inner reinforcing ribs 215 are projected. The reinforcing elements 213-215 form linear thickened parts of the front wall 21, which are depicted in detail in FIG. 3 showing a fragmentary view of the central part 211 of the terminal front wall 21 from the inside of the body 2.

In the internal reinforcing ring 214, a positioning recess 216 is formed with the inner diameter fitted to the outside diameter of the discharge tube 32 of the container 3, wherein the inner diameter is also substantially larger than the diameter of the discharge opening 212 located in the central part of the recess 216. In the positioning recess 216, the end part of the discharge tube 32 of the container 3 is placed such that its outlet 31 is directly fluidly connected to the discharge opening 212. The positioning recess 216 serves for providing an appropriate positioning the outlet 31 with respect to the discharge opening 212, and the bottom of the positioning recess 216 forms a stop surface for the discharge tube 32 when the container 3 moves toward the terminal front wall 21 for releasing the freezing agent from the container 3.

The body end part 23 has a form of a convex shell dome with a truncated top part that surrounds the discharge opening 212 of the terminal front wall 21 on the outside of the wall 21. The body end part 23 comprises an exhaust opening 231 located centrally on the axis O of the discharge opening 212 of the central part 211 at a certain distance outwards from this discharge opening 212. The exhaust opening 231 of the body end part 23 lies in the plane of the flat central part 211 of the terminal front wall 21. The body end part 23 comprises two vent openings 232 formed in its side surface oppositely to each other. The vent openings 232 lie in the plane that is perpendicular to the longitudinal axis O and intersects the side surface of the terminal front wall 21. The body end part 23 is connected to the body 2 by means of a detachable connection means including first catches 233 protruding inwards from its edges and engaging in the corresponding first latching openings 24 formed in the body 2.

The terminal rear wall 22 is provided with a sleeve 221 apt for connecting this wall 22 to the body 2. Two second catches 222 project inwards from the edge of the sleeve 221 and hooked into the corresponding second latching openings 25 formed in the body 2. The circumferential lengths of the second latching openings 25 are several times longer than the circumferential lengths of the second catches 222 of the terminal rear wall 22, so that it is possible to rotate the rear wall 22 with respect to the body 2 about the longitudinal axis O of the body 2 in the state of a connection of these elements 2, 22 with each other. Therefore the second latching openings 25 are in the form of longitudinal latching grooves extending in a plane perpendicular to the longitudinal axis O.

In the terminal rear wall 22, a locking groove 26 is formed, in which a button 223 movable in the axis O of the body 2 is located, constituting the actuating element of the device 1. The button 223 is an integral part of the terminal rear wall 22 and is connected to it by means of a thin deformable material bridge 224 constituting a strip hinge on which the button 223 rotates. Rotating the button 223 on the bridge 224 into the interior of the body 2 (as indicated by the arrow in FIG. 2) causes this button presses down on the container 3 and moves the container 3 toward the front wall 21. Since the discharge tube 32 of the container 3 remains stationary upon its, support against the front wall 21, moving the container 3 due to pressing thereon by the button 223 causes the discharge tube 32 to become inserted deeper inside the container 3 to open the exhaust valve of the container 3 what finally results in discharging the freezing means through the outlet 31 of the container 3, and then successively through the discharge opening 212 of the front wall 21 to the area above the exhaust opening 231 of the body end part 23, in which a neutralizing ectoparasite is placed.

The button 223 is equipped with a lock blocking its movement depending on the angular orientation of the rear wall 22 with respect to the body 2. A locking projection 225 protrudes from the button 223 into a circumferential locking groove 26 extending circumferentially in a plane perpendicular to the longitudinal axis O of the body 2. An internal edge 261 of the groove 26 forms a retaining edge for the movement of the locking projection 225 into the body 2 and comprises two sections with different distances from the wall 21. Whereas an external edge 262 of the groove 26 preventing the button 223 from slipping outwards runs along its entire length at the same distance from the wall 21. Thus the locking groove 26 has two sections with different widths. The variable angular orientation of the rear wall 22 with respect to the body 2 determines the relative angular orientation of the locking projection 225 with respect to the sections of the internal edge 261 of the locking groove 26.

In a case where the locking projection 225 is in the region of the internal edge 261 that is proximal to the front wall 21 (i.e., in the region with the greater width of the locking groove 26), it is enabled to move the button 223 towards the container 3 to activate the device 1. However, in the case where the locking projection 225 is in the region of the internal edge 261 further away from the front wall 21 (i.e., in the region with the smaller width of the locking groove 26), resting the locking projection 225 against this edge 261 prevents the button 223 from moving toward the container 3 and thus prevents the device 1 from becoming activated.

In FIG. 2, dashed lines illustrate the circumferential shape of the second latching openings 25 and the locking groove 26 and its internal edge 261 and its external edge 262. In order to better visualize the matching of the second catches 222 to the corresponding second latching openings 25 and the matching of the locking projection 225 to the locking groove 26, in the cross-sectional view of FIG. 2 the elements 222 are shown in an angular position displaced from their angular position presented in FIG. 1. Owing to this in a one figure the insertion states of all elements 222, 225 into the corresponding grooves 25, 26 may be shown.

The disclosed embodiments should not be regarded as exhaustive, and some details of the drawing are shown only schematically in order to better illustrate the invention, the essence of which has been characterized in the claims.

LIST OF REFERENCE NUMERALS 1 device
2 body
21 terminal front wall
211 central part
212 discharge opening
213 external reinforcing ring
214 internal reinforcing ring
215 reinforcing rib
216 positioning recess
22 terminal rear wall
221 sleeve
222 second catches
223 actuating element (button)
224 deformable element (material bridge)
225 locking projection
226 opening (of the wall 22)
23 body end part
231 exhaust opening
232 vent opening
233 first catches
24 first latching openings
second latching openings
26 locking groove
261 internal edge (of the groove 26)
262 external edge (of the groove 26)
3 container
31 outlet
32 discharge tube

The invention claimed is:

1. A device for neutralizing ectoparasites, comprising
a container containing a neutralizing freezing medium, preferably an aerosol cooling medium, in particular preferably an aerosol of a mixture of isohexadecane, isopropyl myristate and cooling medium, preferably 1,1,1,2-tetrafluoroethane,
a body, in which the container is located, and which comprises
a terminal front wall with a discharge opening located on the axis (O) of the outlet of the container and
a terminal rear wall,
a body end part in a form of a convex shell element that encloses the discharge opening of the terminal front wall on the external side of this wall and comprises an exhaust opening located on the axis of the discharge opening of the terminal front wall at a distance from this discharge opening and at least one vent opening, characterized in that
the terminal rear wall of the body comprises an actuating element provided with a lock, wherein
the terminal rear wall is a separate individual element detachably connected to the body so as to enable rotating the terminal rear wall relative to the body around the longitudinal axis of the body, wherein the locking status of said lock is determined by the angular orientation of the terminal rear wall relative to the body.

2. The device according to claim 1, characterized in that the outlet of the container is located at the end of a discharge tube of the container that is situated in a positioning recess formed in the terminal front wall of the body.

3. The device according to claim 1, characterized in that reinforcing elements, preferably reinforcing ribs and/or at least one reinforcing ring, are formed in the terminal front wall over the area around the discharge opening.

4. The device according to claim 1, characterized in that the body end part has a form of a separate individual element detachably connected to the body.

5. The device according to claim 1, characterized in that the terminal front wall of the body is convex, and preferably has a form of a truncated cone with a concave side surface and includes a central part with the discharge opening, wherein the central part is preferably flat, and the body end part has a form of a dome having a truncated top part and the central exhaust opening lying in the plane of the central part of the terminal front wall of the body.

6. The device according to any one of claim 1, characterized in that the actuating element is arranged in the terminal rear wall and connected to the terminal rear wall by a deformable element, wherein the actuating element is preferably an integral part of the terminal rear wall connected therewith by a material bridge.

7. The device according to claim 2, characterized in that reinforcing elements, preferably reinforcing ribs and/or at least one reinforcing ring, are formed in the terminal front wall over the area around the discharge opening.

8. The device according to claim 2, characterized in that the body end part has a form of a separate individual element detachably connected to the body.

9. The device according to claim 2, characterized in that the terminal front wall of the body is convex, and preferably has a form of a truncated cone with a concave side surface and includes a central part with the discharge opening, wherein the central part is preferably flat, and the body end part has a form of a dome having a truncated top part and the central exhaust opening lying in the plane of the central part of the terminal front wall of the body.

10. The device according to claim 2, characterized in that the actuating element is arranged in the terminal rear wall and connected to the terminal rear wall by a deformable element, wherein the actuating element is preferably an integral part of the terminal rear wall connected therewith by a material bridge.

11. The device according to claim 3, characterized in that the body end part has a form of a separate individual element detachably connected to the body.

12. The device according to claim 3, characterized in that the terminal front wall of the body is convex, and preferably has a form of a truncated cone with a concave side surface and includes a central part with the discharge opening, wherein the central part is preferably flat, and the body end part has a form of a dome having a truncated top part and the central exhaust opening lying in the plane of the central part of the terminal front wall of the body.

13. The device according to claim 3, characterized in that the actuating element is arranged in the terminal rear wall and connected to the terminal rear wall by a deformable element, wherein the actuating element is preferably an integral part of the terminal rear wall connected therewith by a material bridge.

14. The device according to claim 4, characterized in that the terminal front wall of the body is convex, and preferably has a form of a truncated cone with a concave side surface and includes a central part with the discharge opening, wherein the central part is preferably flat, and the body end part has a form of a dome having a truncated top part and the central exhaust opening lying in the plane of the central part of the terminal front wall of the body.

15. The device according to claim 4, characterized in that the actuating element is arranged in the terminal rear wall and connected to the terminal rear wall by a deformable element, wherein the actuating element is preferably an integral part of the terminal rear wall connected therewith by a material bridge.

16. The device according to claim 5, characterized in that the actuating element is arranged in the terminal rear wall and connected to the terminal rear wall by a deformable element, wherein the actuating element is preferably an integral part of the terminal rear wall connected therewith by a material bridge.

17. The device according to claim 2, characterized in that reinforcing elements, preferably reinforcing ribs and/or at least one reinforcing ring, are formed in the terminal front wall over the area around the discharge opening; and
   the body end part has a form of a separate individual element detachably connected to the body.

18. The device according to claim 17, characterized in that the terminal front wall of the body is convex, and preferably has a form of a truncated cone with a concave side surface and includes a central part with the discharge opening, wherein the central part is preferably flat, and the body end part has a form of a dome having a truncated top part and the central exhaust opening lying in the plane of the central part of the terminal front wall of the body.

19. The device according to claim 18, characterized in that the actuating element is arranged in the terminal rear wall and connected to the terminal rear wall by a deformable element, wherein the actuating element is preferably an integral part of the terminal rear wall connected therewith by a material bridge.

20. The device according to claim 17, characterized in that the actuating element is arranged in the terminal rear wall and connected to the terminal rear wall by a deformable element, wherein the actuating element is preferably an integral part of the terminal rear wall connected therewith by a material bridge.

* * * * *